US008655036B2

(12) United States Patent
Valadez et al.

(10) Patent No.: US 8,655,036 B2
(45) Date of Patent: Feb. 18, 2014

(54) PRESENTATION OF LOCATIONS IN MEDICAL DIAGNOSIS

(75) Inventors: Gerardo Hermosillo Valadez, West Chester, PA (US); Luca Bogoni, Philadelphia, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 245 days.

(21) Appl. No.: 13/114,072

(22) Filed: May 24, 2011

(65) Prior Publication Data

US 2012/0207369 A1 Aug. 16, 2012

Related U.S. Application Data

(60) Provisional application No. 61/442,338, filed on Feb. 14, 2011.

(51) Int. Cl.
*G06K 9/00* (2006.01)
(52) U.S. Cl.
USPC ................................. 382/128; 128/922; 378/4
(58) Field of Classification Search
USPC .............. 382/100, 128, 129, 130, 131, 132; 128/922; 378/4–27
See application file for complete search history.

(56) References Cited

U.S. PATENT DOCUMENTS

| 5,782,762 | A  | * | 7/1998 | Vining | 600/407 |
|---|---|---|---|---|---|
| 6,819,785 | B1 | * | 11/2004 | Vining et al. | 382/128 |
| 7,343,036 | B2 | * | 3/2008 | Kleen et al. | 382/154 |
| 2004/0249291 | A1 | * | 12/2004 | Honda et al. | 600/476 |
| 2006/0023966 | A1 |  | 2/2006 | Vining |  |
| 2006/0215896 | A1 | * | 9/2006 | Sirohey et al. | 382/131 |
| 2007/0122016 | A1 | * | 5/2007 | Brejl et al. | 382/128 |
| 2008/0050043 | A1 | * | 2/2008 | Hermosillo Valadez et al. | 382/294 |
| 2008/0187202 | A1 |  | 8/2008 | Qian et al. |  |
| 2009/0016589 | A1 |  | 1/2009 | Wolf et al. |  |
| 2009/0263000 | A1 |  | 10/2009 | Shinagawa et al. |  |
| 2010/0150416 | A1 | * | 6/2010 | Kim et al. | 382/128 |
| 2011/0044534 | A1 |  | 2/2011 | Dewan et al. |  |

FOREIGN PATENT DOCUMENTS

WO 2009/109205 9/2009

OTHER PUBLICATIONS

Ronald M Summers, "Image gallery: A tool for rapid endobronchial lesion detection and display using virtual bronchoscopy", Journal of Digital Imaging, The Journal of the Society for Computer Applications in Radiology, Springer-Verlage, NE, vol. 11, No. 1, Aug. 1, 1998, pp. 53-55.
PCT Search Report of International Application No. PCT/US2011/037895 dated Oct. 12, 2011.

* cited by examiner

*Primary Examiner* — Anand Bhatnagar
(74) *Attorney, Agent, or Firm* — Peter R. Withstandley

(57) ABSTRACT

Locations, such as computer assisted detection marks, are presented in medical imaging diagnosis, such as for colon computed tomography diagnosis. To avoid fly-through and/or to assist in more rapid and thorough review of CAD marks, a summary of a plurality of detected candidates is pre-computed and presented to the user in a single collection. For example, a single display or screen view includes a gallery of images for different candidates. These pre-computed images are displayed on the screen, allowing the user to quickly identify locations of interest and rule out other locations. The summary may be used for navigation outside the CAD context, such as presenting different portions of an organ to be viewed.

9 Claims, 6 Drawing Sheets

| MARKER ID | LOCATION | DIAMETER | HEIGHT | CORE TISSUE | GALLERY | |
|---|---|---|---|---|---|---|
| 1a | RECTUM | 6.5 | 5 | MUSCLE | | |
| 2a | ASCENDING | 10 | 7 | MUSCLE | | |
| 3a | DESCENDING | 6 | 3 | TAG/MUSCLE | | |
| 4b | RECTUM | 7.5 | 4.5 | MUSCLE | | |
| 5b | ASCENDING | 12 | 7.5 | MUSCLE | | |
| 6b | TRANSVERSE | 5.5 | 2 | FAT/MUSCLE | | |

FIG. 4

PRESENTATION OF LOCATIONS IN MEDICAL DIAGNOSIS

CROSS-REFERENCE TO RELATED APPLICATIONS

The present patent document claims the benefit of the filing date under 35 U.S.C. §119(e) of Provisional U.S. Patent Application Ser. No. 61/442,338, filed Feb. 14, 2011, which is hereby incorporated by reference.

BACKGROUND

The field of medical imaging has seen significant advances since the time X-Rays were first used to determine anatomical abnormalities. Medical imaging hardware has progressed in the form of newer machines such as Medical Resonance imaging (MRI) scanners, Computed Axial Tomography (CAT) scanners, etc. Because of large amount of image data generated by such modern medical scanners, there has been and remains a need for developing image processing techniques that can automate some or all of the processes to determine the presence of anatomical abnormalities in scanned medical images.

Recognizing anatomical structures within digitized medical images presents multiple challenges. For example, a first concern relates to the accuracy of recognition of anatomical structures within an image. A second area of concern is the speed of recognition. Because medical images are an aid for a doctor to diagnose a disease or condition, the speed with which an image can be processed and structures within that image recognized can be of the utmost importance to the doctor reaching an early diagnosis. Hence, there is a need for improving recognition techniques that provide accurate and fast recognition of anatomical structures and possible abnormalities in medical images.

Digital medical images are constructed using raw image data obtained from a scanner, for example, a CAT scanner, MRI, etc. Digital medical images are typically either a two-dimensional ("2-D") image made of pixel elements or a three-dimensional ("3-D") image made of volume elements ("voxels"). Such 2-D or 3-D images are processed using medical image recognition techniques to determine the presence of anatomical structures such as cysts, tumors, polyps, etc. Given the amount of image data generated by any given image scan; it is preferable that an automatic technique should point out anatomical features in the selected regions of an image to a doctor for further diagnosis of any disease or condition.

One general method of automatic image processing employs feature based recognition techniques to determine the presence of anatomical structures in medical images. However, feature based recognition techniques can suffer from accuracy problems.

Automatic image processing and recognition of structures within a medical image is generally referred to as Computer-Aided Detection (CAD). A CAD system can process medical images and identify anatomical structures including possible abnormalities for further review. Such possible abnormalities are often called candidates and are considered to be generated by the CAD system based upon the medical images.

Computer Assisted Detection (CAD) assists medical professionals in diagnosis of patients based on data. For example, CAD can assist in identifying and/or diagnosing suspect locations in a medical image. CAD may operate as a first or second reviewer, e.g., providing more efficient and reliable second review. One use case is that CAD can be used for computed tomography (CT) colonography.

In CT colonography an interior view of the colon (i.e., the large intestine) is obtained using CT scanning. CT colonography allows viewing of the colon without a more invasive procedure where an endoscope is inserted into the rectum. CT colonography is a valuable tool for early detection of colon polyps that may later turn into cancer. From CT acquisitions of the patient's abdomen, radiologists are able to find polyps attached to the colon wall by inspecting two-dimensional reconstructions of individual planes of the image in different orientations or by performing a "virtual colonoscopy." For virtual colonoscopy, a virtual fly-through of the entire interior of the colon is performed. The fly-through is from the rectum to the cecum, much in a way that would mimic an optical colonoscopy. However, virtual fly-through may be time consuming.

CAD systems are used as a second-reader after the fly-through to provide pointers to locations that the system determines to be polypoid in morphology and texture. The user enables the CAD marks after an initial unaided evaluation of the CT images. When enabled, the application shows marks labeled with an alpha-numeric code which appear both on a global three-dimensional view of the colon with arrows pointing to individual locations and as a list. Upon selection of one of the marks, the application automatically jumps to the corresponding location for the radiologist to evaluate. FIG. 1 shows an example of a CAD mark labeled 1a in a global three-dimensional view of the colon. When the user selects the marker 1a from the list of available CAD marks, the application sets the virtual endoscopic camera to the location of the CAD mark and sets the cross-bars of the two-dimensional reconstructions at the same location. Two-dimensional reconstructions and a three-dimensional endoscopic view are then rendered as shown in FIG. 2. However, this rendering may be time consuming. For a user to review all the candidates requires a substantial number of selections and then renderings, resulting in further delays.

SUMMARY

In various embodiments, systems, methods, instructions, and computer readable media are provided for presentation of locations, such as computer assisted detection marks, in medical imaging diagnosis. For example, computer assisted detection marks are presented for colon computed tomography diagnosis. To avoid fly-through analysis and/or to assist in more rapid and thorough review of CAD marks, a summary of a plurality of detected candidates is pre-computed and presented to the user as a single collection. For example, a single display or screen view includes a gallery of images for different candidates. These pre-computed images are displayed on the screen, allowing the user to quickly identify locations of interest and rule out other locations. The summary may be used for navigation outside the CAD context, such as presenting different portions of an organ to be viewed.

In a first aspect, a non-transitory computer readable storage medium has stored therein data representing instructions executable by a programmed processor for presentation of computer assisted detection marks in colon computed tomography diagnosis. The instructions include receiving a first plurality of images representing a first computer assisted detected (CAD) candicate in a colon of a patient, the images of the first plurality representing the first computer assisted detected candidate from different views, receiving a second plurality of images representing a second computer assisted detected candidate in the colon of the patient, the images of the second plurality representing the second CAD candidate from different views, and presenting a gallery of the first and second pluralities of images substantially simultaneously on a display.

In a second aspect, a method is provided for presentation of locations in medical imaging diagnosis. A processor displays multiple data points for each of a plurality of locations in a single view. The locations are for a same anatomy of a same patient from a same imaging session. The display occurs without a fly-through presentation for the imaging session and prior to the display. The user navigates between the locations without the fly-through presentation for the imaging session occurring prior to the navigating. At least one image for a first of the locations is displayed in response to the navigating.

In a third aspect, a system is provided for presentation of locations in medical imaging diagnosis. A processor is configured to generate a summary of positions within a patient organ. The summary includes images of the positions. The images are in a list arrangement. A display is configured to display the summary where the images in the list arrangement for multiple of the positions are presented at a same time.

Any one or more of the aspects described above may be used alone or in combination. These and other aspects, features and advantages will become apparent from the following detailed description, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIGS. 4-6 are different embodiments of presentations of multiple candidate computer assisted detection locations;

DETAILED DESCRIPTION OF THE DISCLOSURE

Figure 1:
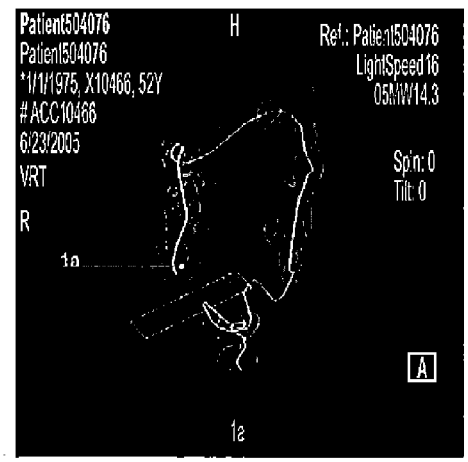
FIG. 1 is a medical image showing a colon with a CAD mark.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention.

While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of a radiosurgery or radiotherapy procedure, which may include times when the radiation source is either on or off. From time to time, for convenience of description, CT imaging data may be used herein as an exemplary imaging modality. It will be appreciated, however, that data from any type of imaging modality including but not limited to X-Ray radiographs, MRI, CT, PET (positron emission tomography), PET-CT, SPECT, SPECT-CT, MR-PET, 3D ultrasound images or the like may also be used in various embodiments of the invention.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from R3 to R or R7, the methods of the inventions are not limited to such images, and can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

In a list of labeled marks (e.g., 1a, 2d, 3c, . . . , 4a) referenced to a global image (see FIG. 1), the user does not receive information other than location in the colon as judged from the global three-dimensional rendering and the CAD-mark arrows. The CAD marks may be false positives, so the process of selecting each mark and rendering the three-dimensional and two-dimensional views at run-time in response to each selection may be time-consuming.

Several paradigms of presentation of the CAD marks or other locations are provided for more efficient review. A plurality of CAD marks are received or detected, Different data points are provided for each of the candidate CAD locations. The data points may be images, such as thumbnail two and/or three-dimensional views of each candidate CAD location. The data points may be quantities calculated from the candidate CAD locations. For example, the locations that lie on the surface of a polypoid structure are identified and may be segmented. Both an intrinsic direction that goes from the tip of the polyp to its base (i.e., polyp gravity) as well as the tip location itself may be identified. From there, the polyp base may be defined which in turn allows estimation of the polyp height, diameter, enclosed volume, solid angle, or other characteristics rendered computable from the polyp segmentation.

Identification of the polyp or other structure may be used to determine one or more view points for two-dimensional images and/or three-dimensional renderings. Galleries of images showing the polypoid structure, appearance and context in addition to the relevant properties of the finding may be automatically pre-computed and stored, for instance, in the form of a table. The radiologist may evaluate and assess the relevance of the CAD marks at a glance from the table and/or image gallery.

A list of quantities and/or galleries may allow the user to jump to corresponding locations for enlarged viewing of relevant candidates by clicking in corresponding information in the list or gallery (e.g., selecting a row). A different monitor may be used to display and control a three-dimensional rendering and/or two-dimensional reconstructions (e.g., axial, coronal, and sagittal reconstructions). The user may select or deselect candidates based on the gallery and/or quantities. The summary or consolidated collection may be used for insertion or deletion of findings.

In the examples below, CAD for a colon is used. A given patient is scanned with computed tomography, creating data representing the colon of the patient from two views—prone and supine. These two views may be from scans at different times but during a same imaging session. An imaging session corresponds to the scanning a patient during a given visit. The data for one or more images may be generated during the imaging session. The data may be used to generate images at times other than the imaging session. Diagnosis may occur during the imaging session, such as while the patient waits after a scan but before departure, or may occur at other subsequent times.

In other embodiments, CAD is applied to a different organ than the colon. In other embodiments, different imaging modalities are used, such as ultrasound, magnetic resonance, or nuclear imaging. Different views or types of data may be acquired during one or more imaging sessions. In yet other embodiments, candidates or locations are manually identified rather than detected as part of CAD.

Rather than presenting images for CAD review, the images may be presented to assist in user navigation. An organ is divided into different portions or segments automatically or manually. Groups of images are provided for each portion or segment in a single presentation. The user may navigate to images of any portion or segment of interest by selecting the presented images.

Figure 3:
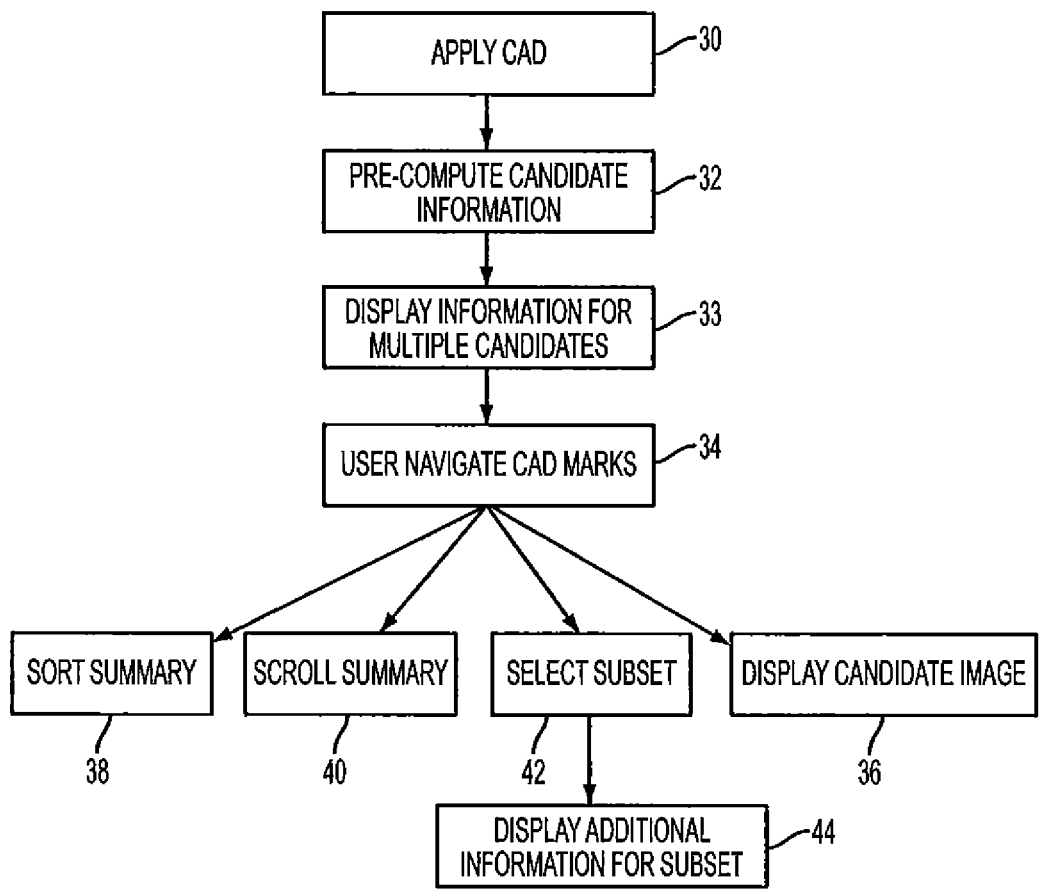
FIG. 3 is a flow chart diagram of one embodiment of a method for presentation of computer assisted detection marks in medical imaging diagnosis.

FIG. 3 shows one embodiment on a method for presentation of computer assisted detection marks in medical imaging diagnosis. The method uses the system of FIG. 8 or a different system. Additional, different or fewer acts than shown in FIG. 3 may be used. For example, act 30 is not performed, and the candidate CAD locations are instead acquired from a user, transfer, or storage. As another example, any one or more of acts 34-44 are not performed.

In act 30, a computer assisted detection (CAD) algorithm is applied. The CAD algorithm is configured to detect a condition of a patient or other information from patient information. Any CAD algorithm may be used. The CAD algorithm may be for detecting any condition, such as polyps, cancer, or nodules. The CAD algorithm uses filtering, machine-trained classifiers, matching, correlation, gradient processing, combinations thereof, or other approaches to detect the condition.

The classifier has any sensitivity level. In one embodiment, the classifier has high sensitivity, making the CAD algorithm more likely detect locations. Where initial analysis by a medical professional may be skipped or avoided, detecting a greater number of candidates at the risk of including more false positives is desired as compared to fewer candidates but with more of the candidates being true positives.

A processor applies the CAD to patient information, such as data representing a two or three-dimensional region of the patient. In the colon example, image information or data from a CT scan of the region of the patient is used without other types of information. Any type of patient data may be acquired. The patient information is acquired using any now known or latter developed techniques, such as scanning, imaging, laboratory tests, patient interview, physician notes, or other approaches. The data is manually entered or retrieved by a processor. For example, a patient record is data mined. As another example, an image is acquired from a picture archiving and communications system or from a scanner. The patient information may be acquired from storage or previous visits or may be acquired during a current or on-going visit. The patient information may represent data acquired at different times, such as a sequence of images or a video.

The CAD algorithm determines the locations of one or more candidates. For example, the locations of tens of candidates are determined. In the example CT colonoscopy embodiment, fifteen or other number of candidate CAD locations with the highest probabilities of being polyps are selected for each CT view. Two sets of candidates are output, one for the prone view and another for the supine view of the CT scan. Any criteria for selection may be used, such as probabilities associated with a machine-trained CAD algorithm.

The candidate CAD locations are for the same anatomy of a same patient. In one embodiment, the candidate CAD locations are detected locations for the same condition, such as detected possible polyps. In other embodiments, the candidate CAD locations are from the same organ (e.g., colon), but different conditions (e.g., stool or tags detected separately than polyps). The candidate CAD locations are to be reviewed to diagnosis the condition, so possible or likely candidates showing the condition in the same organ are identified.

The candidate CAD locations are for the same patient. The organ or organs of the patient are scanned during an imaging session. The candidate CAD locations are detected from the scan data acquired during the imaging session for that patient. In alternative embodiments, the candidate CAD locations may be detected from data from different imaging sessions, such as candidates from different scans performed days, weeks, months, or years apart.

In act 32, one or more images are pre-computed. For each of the candidates, at least one image is generated as a data point. In alternative embodiments, characteristics, quantities, properties or other information for the candidate CAD locations are pre-computed in addition to or as an alternative to images.

The image may be a two-dimensional view, such as a cross section through the candidate location. The orientation of the cross section may be based on the patient orientation, organ orientation, or detected condition orientation (e.g., the orientation of the candidate polyp). More than one two-dimensional view may be generated, such as a multi-planar reconstruction of two or three images.

The image may be a three-dimensional view, such as a surface or projection rendering of the candidate location. The viewer location for rendering may be upstream or downstream of the candidate location, looking along the colon axis or towards the candidate. In other examples, the viewer location is spaced from the candidate, looking at the candidate, along a line orthogonal to the organ wall or orientation based on the candidate. More than one three-dimensional view may be generated.

Figure 5:
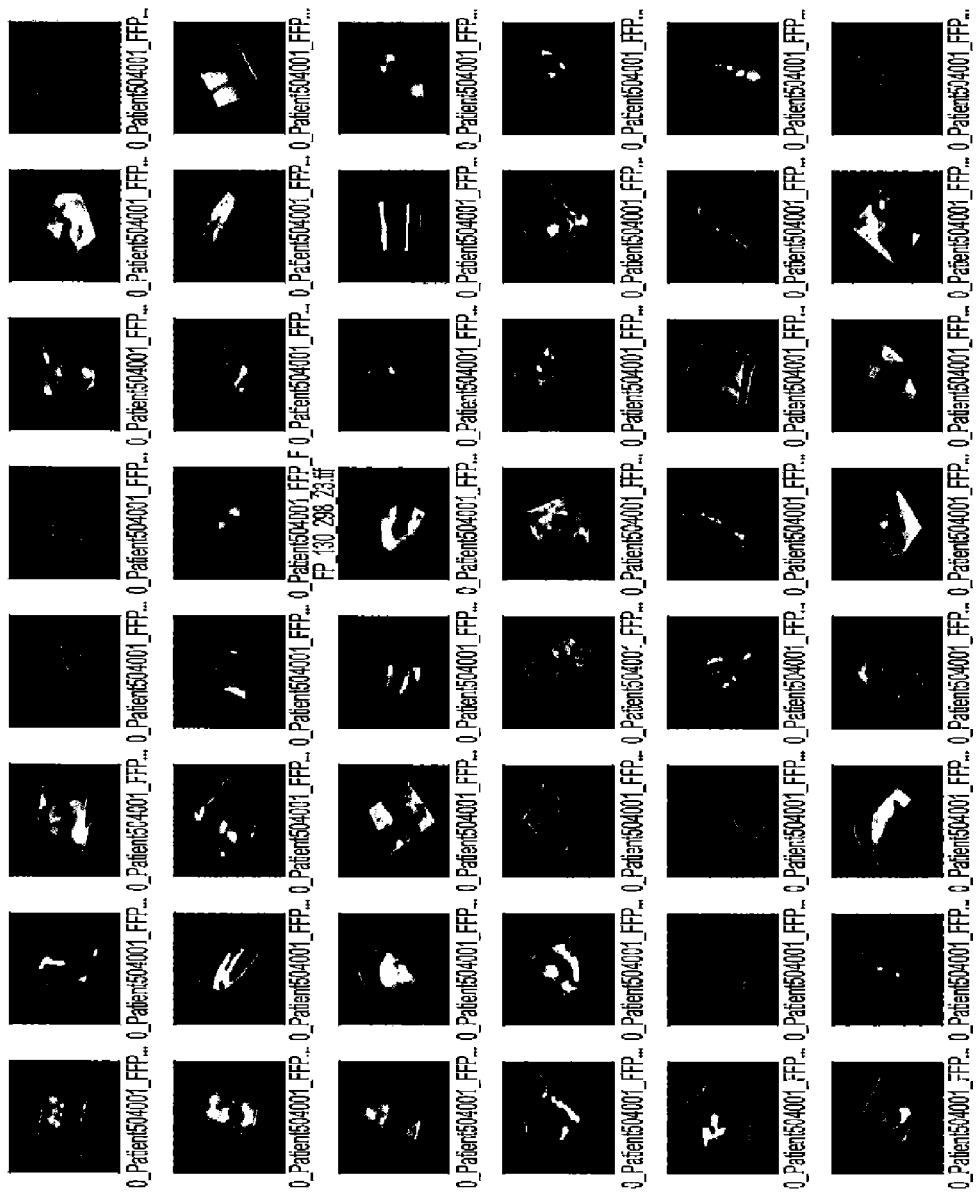
Figure 6:

The image or images are reduced resolution. For example, the scan data is decimated prior to image generation. Alternatively, the image is generated and then decimated. The image or images are sized to allow a plurality of images, such as five or more, to be viewed on a same display device at a same time. FIGS. 4-6 show examples of such images. The images are presented as thumbnails rather than full size images. For example, FIG. 6 shows smaller, such as thumbnail, images on the right half (e.g., on one monitor) and larger images on the left half (e.g., on another monitor). The larger images are small as compared to generating a single image on a given monitor, but large enough that only one, two, four, six or other limited number (relative to any gallery of smaller images) of such images may be presented simultaneously. The smaller images pre-computed in act 32 may have various sizes, such as allowing tens or even hundreds of such images to be presented simultaneously on a given display.

The range or region size represented by the image is based on the size of the candidate or a predetermined size. The region size is a close up showing the possible polyp or other condition with surrounding tissue. For example, FIGS. 4-6 show various close-ups of candidates. The detected condition is shown in a majority of the image, but may be shown in less area to provide more context.

In other embodiments, one or more two or three-dimensional images represent larger regions, such as a majority or entirety of the organ. For example, FIG. 1 shows an image of the entirety of the colon. The image of FIG. 1 may be pre-computed, but on a smaller scale or resolution.

The images may be static or animated, such as a three-dimensional rendering where the viewing perspective changes position in a loop. The two-dimensional images may be static or may be animated by switching between different cross-sectional views.

The pre-computation of act 32 occurs prior to display of the images for the different candidates in act 33. The images are generated prior to user selection of a candidate location. Rather than generating the images when the user selects a candidate location from a list or global view, the images are generated to be used for the initial selection for viewing larger images. The larger images are pre-computed or are computed after and in response to selection as needed.

In alternative or additional embodiments, images are not pre-computed. Instead, other information is pre-computed. For example, quantities for different characteristics (e.g., volume, surface area, diameter, height, base area, or shape) are pre-computed. These data points with or without images as data points are computed prior to presentation to the user of information for multiple candidates, but may be computed on the fly in other embodiments.

In act 33, multiple data points are displayed for each of a plurality of candidate computer assisted detection (CAD) locations. A processor generates a display or view of multiple data points. Each data point is a type of information for the candidate CAD location. For example, one type of data point is a two-dimensional image, three-dimensional image, property, or a quantity. Any number of data points may be provided for each candidate location.

The data points for a plurality of candidate CAD locations are provided at a substantially same time. Substantially accounts for processes that may not occur simultaneously but have the appearance to a human user of being simultaneous. For example, raster processes may cause display of one part or even an entire data point for one candidate CAD location prior to another in generating a single view on a display. As another example, different information may be temporally interleaved at a rate sufficient that a user perceives the display to be simultaneous.

The processor displays the data points in a single view or other single presentation. The single view is on a given monitor or other display device. The single view is the overall image or view presented on the display device at a given time. Where multiple display devices are provided, different single views are provided at a given time on the devices.

The data points are displayed. Any display may be used, such as displaying on a screen or printing on a report. The display may occur during a patient visit or imaging session. For example, an image is acquired during a patient visit to medical offices. The CAD algorithm is applied and the display of the data points for multiple candidate locations is output during the visit. While the patient is at the medical office, the medical personal may review the results, reach a conclusion or diagnosis, and review the results with the patient. Further scanning, imaging, tests, questions or other medical procedures may occur, in part, based on the results without requiring another patient visit. In other embodiments, the display occurs after a patient has left.

The data points are displayed in a table, chart, graph, image gallery, text, or other format. For example, multiple images, at least one for each candidate location, are displayed in a single view. The small images provide context for a plurality of the candidate CAD locations. The single view provides information for multiple candidate CAD locations viewable at a same time, without further navigation.

The data points may be provided in a single collection or document as viewed. Some navigation, such as scrolling, tabbing, or page flipping, may be required to view the entire collection or document, but without having to create more information, such as render further images or compile further information. The data points are collected and used to form the single view, collection, report, or document. The single view, collection, report, or document is presented to the user such that the data points for multiple candidate CAD locations are shown prior to navigation to view specific candidate CAD locations. The user may view the summary information for the collected candidate CAD locations without having to individually view specific candidate CAD locations.

In the colonoscopy example, multiple data points for two or more candidate locations are presented to the user. In one embodiment, five, ten, fifteen, eighteen, twenty three, or other number of candidate CAD locations are used for each CT view (e.g., 15 for prone and 15 for supine). The data points for these possible CAD polyps are presented to the user substantially simultaneously on the display. For example, at least one image focused on each candidate CAD location is presented in a same view or document. The image is generated from the CT data.

In one embodiment, the data points include images. A gallery of images is displayed. The gallery is a collection of multiple images, such as thumbnail images or images sized to allow the gallery to be displayed in the single view or other single presentation. The images may be visually spaced apart or separated, or may be displayed immediately adjacent to each other. The images of the gallery represent the candidate CAD locations.

The images may be local images, such as being focused on the detected feature. In the colonoscopy example, a majority of each local image shows the possible polyp detected by the CAD algorithm.

The images may be global images, such as representing the entire or a majority of the organ. For example, the image shown in FIG. 1 is used for at least one of the images of the gallery. A global image for each candidate CAD location is provided to show the different locations without the clutter of showing all or multiple locations on one global image.

The gallery is presented substantially simultaneously. The images of the gallery are provided in the same view, document, report or other presentation. For example, the user may view the display and see the images on the same screen. FIGS. 4-6 show galleries in a same view or on a same screen. In the example of FIG. 6, images for five candidate locations are shown on a monitor (e.g., right side). With fifteen candidate CAD locations in the summary of one example, scrolling, tabbing or page flipping may be used to view the other candidate CAD locations in the same report or document. For example, three single view pages are provided in the single summary document. The single summary document is prepared with the pre-computed data points and available to the user for review without further computation of data points.

The images or other data points are displayed as groups. The data points for each candidate location are grouped. A border, spacing, color, or other indication separates the data points of the different groups. For example, FIGS. 4 and 6 show the data points grouped by rows. The data points in each row are for a same candidate CAD location. Different rows represent different candidate locations. Other groupings than by rows may be used, such as by column or by quad.

For each group or candidate CAD location, any number of data points may be presented. FIG. 5 shows a single data point for each candidate CAD location, so the groupings are the separate images. None, one, or multiple images may be provided for each candidate CAD location. FIG. 4 shows two thumbnail images for each candidate CAD location. FIG. 6 shows six small images for each candidate CAD location. None, one, or multiple quantities characterizing the detected feature may be provided for each candidate CAD location. FIGS. 5 and 6 shows no quantities for the five candidate CAD locations. FIG. 4 shows four characterizations. The characterizations include two types of quantities (e.g., height and diameter), a textual location description, and a classification (e.g., core tissue). Fewer, more, or different data points may be used.

FIG. 4 shows one presentation of a single view, single document, or other collection of data points for multiple candidate CAD locations. A table of polyp-properties with an image gallery is presented to the user. Instead of a mere list of marker labels, the user is presented with a table showing relevant properties of the structures pointed to by the CAD marks. In this example, the properties include the location in the colon, the diameter and height, the type of tissue at the structure core and a gallery of images. The images are automatically generated and aligned relative to a standard viewpoint, such as from the top of the possible polyp as defined by a gravity vector or center axis of the possible polyp. At a simple glance of this table, the user already has useful information that may allow decisions regarding which of the CAD marks to visit or not, and in which order. In alternative embodiments, the table of FIG. 4 is provided without the gallery of images.

By viewing this summary table in one view or one document, the user may determine useful information that could save significant time. For example, markers 2a and 5b appear to be the same polyp detected twice by the CAD algorithm. This polyp appears quite conspicuous, so the user probably already noticed the polyp and there may be no need to review the polyp further.

As another example, markers 1a and 4b appear to point to the same structure. This possible polyp is less apparent due to the location being in an inconspicuous zone of the rectum. The user may realize that this polyp was missed during an un-aided read.

The images of the gallery are rendered with a transparent colon wall and tagged material colored in white or grayscale. This rendering shows that marker 3a is a false positive (tagged stool) without having to view enlarged images or navigate to the specific location (e.g., without having to select the candidate CAD location (marker) for further analysis).

As another example, marker 6b is a structure only found in one of the views or candidates. The user may assess from the data points that the value of the automatically-computed diameter is accurate and below a 6 mm threshold. The user may also see that the structure is very flat and has a mostly-fatty core based, in part, on the images and the automatic determination reported in the "Core tissue" column. The user may therefore decide that there is enough evidence of the low-significance of this finding and dismiss the candidate CAD location as a false positive without further review.

FIG. 5 shows another example presentation. A gallery of images for many candidate CAD locations is provided for quick review of a large number of CAD marks. The gallery is of automatically computed thumbnail images. The gallery provides the possibility of reviewing all the possible polyps detected in the Colon in a single two-dimensional screen or view. The CAD algorithm is configured to be overly inclusive for a more complete review. The user relies on the fact that the CAD system is set to an almost perfect sensitivity but at the expense of presenting a large number of marks. In FIG. 5, the CAD system presents forty-eight candidates for which a three-dimensional screenshot has been automatically computed. In each image, the local geometry is not distorted by the rendering as would occur with a "filet" view.

The user may for example dismiss most of the candidates with relative facility, and may decide to further review only a few of the candidates. For example, the last candidate in the lower right is selected for further review. Additional and expanded views may be interactively presented to the user in response to selection or in response to a simple move of the mouse pointer on top of the corresponding finding. This presentation may be useful in a screening scenario, in which most of the patients are expected to be negatives and for which this quick review technique may have a good-enough accuracy for polyp detection on a screening population.

In another example embodiment, the data points are presented as an auto-reporting feature. A limited number of CAD marks are presented to the user. Each finding or candidate CAD location is presented in the form of a full page of a virtual automatic report. This page contains a full set of automatic two- and three-dimensional screenshots which show context and are enlarged as space permits. The page also contains other data points, such as characteristics, measurements, or properties of the candidate. An index or summary page may be included, such as a summary table reporting the finding properties and measurements with or without a gallery of smaller images.

Each page is part of a report or summary, such as being generated in the same document or a common arrangement for the user to scan. The report is provided prior to user navigation to specific ones of the candidate CAD locations. The user reviews each page, dismisses those pages that clearly describe false positives, and further reviews the candidates from the pages considered to be relevant. Any navigation may be used, such as a mouse-click directly on the report's page. After review, the user may complete the report's page with additional comments, corrections and recommendations and save the report as a final analysis for the patient.

FIG. 6 shows another example presentation. The left half of FIG. 6 is on a display device and the right half is on a different display device. The left half shows a single view of five candidate locations. Six images are provided for each candidate location in a gallery. The images are received from a generation process and arranged for presentation. Three of the columns (columns 4-6) are for two-dimensional images of cross-sections along different dimensions through the computer assisted detected (CAD) polyp in a colon of a patient. Another one of the columns (third column) is a three-dimensional rendering of the candidate polyp. In this example, the rendering is from a view point along a line orthogonal to the colon wall or parallel with the gravity vector and through the candidate.

Two other columns (first and second) show more global views. The majority of the colon is represented, and the location of the candidate in the colon is shown. The global image or images may more quickly show the location of the candidate. The first column shows a three-dimensional rendering of the entire colon from a view point outside the patient. The second column shows a cross sectional view through the candidate of a majority of the colon, such as the entire colon.

The images are thumbnail or smaller images showing the candidate polyp from different views. The images are pre-rendered or generated for presentation in the single view or document rather than generated as needed during user navigation. Pre-rendering and generating may save user time and clicking. The presentation of multiple data points, such as the gallery of images with multiple images for each of the candidate CAD locations may improve focus for the user and allow more efficient review. The cross-section information may be used to indicate tissue density (e.g., brighter interior of a candidate may indicate more density and a greater likelihood of being an undesired polyp). The three-dimensional rendering focused on the polyp may provide a quick indication of the shape of the possible polyp. With the overall location information, a user may rapidly determine whether further investigation or image generation is even needed.

Referring again to FIG. 4, the data points may be properties, characteristics, or quantities. This information is displayed to assist the user in more rapid diagnosis than provided by sequentially clicking on and separately analyzing the candidates. Any quantities may be defined and used. Any characteristics or properties may be classified, such as from one or more quantities.

Some example quantities for polyps in the colon are extracted from segmenting the candidate polyp. Any segmentation may be used. In one embodiment, the surface of the possible polyp is identified. Any locations or regions on the surface where the orthogonal intersects a center line (e.g., height line or gravity line) are part of the possible polyp and other locations are colon wall.

Figure 7:
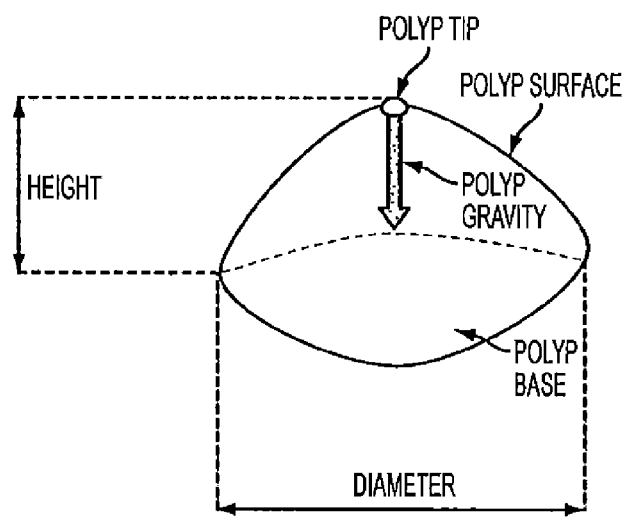
FIG. 7 is an example graphical representation of a polyp.

FIG. 7 graphically represents some example colon polyp quantities. Variations of these definitions are possible. Other measurements may be made. The quantities are measurable from the segmented surface of the possible polyp.

A first example is the intrinsic gravity direction. The normal vector to the polyp surface at a given location is estimated from the intensity at the location. Intensity gradients in different neighborhoods are used to identify the direction of greatest gradient. The orthogonal to that direction is calculated. For an open surface as shown in FIG. 7, the average vector over locations on the surface is an intrinsic direction that points to the surface "opening."

A second example is a polyp tip. The gravity vector defines height for any given surface point. The point at the center of the cluster of surface points that are within a small distance (for example 1 mm) of the highest surface point is defined as the polyp tip. The height is from the surface opening to the center of the polyp tip.

A third example is the polyp base. The polyp base plane is a plane which is orthogonal to the gravity vector and contains surface points that have a height within a small distance (for example 1 mm) from the lowest surface point.

A fourth example is the diameter. The polyp diameter is the largest distance among all possible pairs of points that are within a small distance from the base plane.

A fifth example is the height. The polyp height is the height along the gravity vector from the tip to the base. Alternatively, the polyp height is the difference between the lowest and highest points on the polyp surface.

A sixth example is the volume. The point at which the line parallel to the gravity vector and containing the tip point intersects the base plane is the base center. By including all points belonging to the segments connecting each of the boundary points of the open surface to the base center, the open surface is closed. The internal volume is then calculated.

A seventh example is the solid angle. The solid angle from the base center is computed. The solid angle measures the "portion of the sky" that is covered by the surface as viewed from the origin (e.g., in this case the base center).

An example property or characteristic is the type of the interior tissue. By identifying internal points of the closed volume defined by the base center described above, statistics and properties of the intensities of those points may be computed. One or more statistics, such as average intensity and/or variation in intensity, indicates whether the possible polyp has internal muscle or rather fatty tissue.

The displaying of the data points in act 33 of FIG. 3 occurs without a fly-through presentation prior to the presentation. The user may skip the fly-through and the associated viewing of thousands or millions of images during the fly through where the sensitivity of the CAD algorithm and/or the completeness of the summary are sufficient for the circumstances. The user may avoid performing a fly through during an imaging session, or even for the data acquired during the imaging session. Alternatively, the summary information is presented and then the user performs the fly-through or vice versa.

As an alternative or in addition to fly-through, the data points for the candidate CAD locations are presented. A user may navigate to the various candidate CAD locations by jumping to information at respective locations and skipping review of parts of the colon free of association with the possible polyps. A fly-through may require 5-15 minutes. Navigating through candidates sequentially for a second reader review may require 5 or more minutes. A user may spend 10-20 minutes reviewing images for polyps.

Productivity may be increased by substantially simultaneous presentation of data points for a plurality of candidate CAD locations, such as presentation of an intelligent CAD gallery. The summary information may be reviewed in less than five minutes without a fly-through. The data points include key results or information used to diagnose from the presentation alone. The user may more easily match candidate CAD locations identified in both prone and supine findings. The overall approach, due to the comparative information from different locations and due to the multiple data points provided for each location, may result in maintained or improved sensitivity and specificity verses a conventional approach. The overview of many simultaneous locations may improve prioritization and focus, making at least some results distinguishable at a glance with no clicks or other navigation to view images. For example, common false positive findings, such as tagged stool, the Ileo-Cecal valve and untagged stool, may be easily dismissed by the screenshots or gallery images alone.

In act 34, the user navigates between candidate CAD locations. The navigation is performed without the fly-through presentation for the corresponding imaging session occurring prior to the navigating. The navigation without a fly-through may allow jumping between or to candidate CAD locations without the time required to review all of the colon or other anatomy. The user is directed to only locations of interest and does not have to review other locations. Alternatively, the navigation occurs after a fly-through.

The navigation is in response to user input. The user interacts with the presented information. A user interface is provided to select, change view, scroll, or perform other actions, such as provided in acts 36-42. Different, additional, or fewer types of navigation may be provided.

In act 36, one or more images are displayed for one of the candidate CAD locations. The user navigates by selecting one of the candidate CAD locations. For example, an image, quantity, characteristic, row, group, label, or other data point associated with a given candidate location presented with other candidate locations is selected by the user. In one embodiment, selection is provided merely by positioning a pointer or moving a highlight box. For example, upon the user moving the mouse pointer on top of a gallery cell, the application shows enlarged views of the images in the gallery, as well as complementary screenshots that the CAD algorithm has taken. These enlarged or additional views could include other three-dimensional perspectives, 2D reconstructions for tissue evaluation and enlarged contextual information.

The larger images are pre-computed or are generated as needed. The images are larger versions of the same views presented in the summary or are different views (e.g., include more or less colon context information, are from a different angle, or are from a different plane or cross-section).

Figure 2:
FIG. 2 shows two two-dimensional views and one three-dimensional view of a candidate location.
Figure 2:

In response to the navigating indicating a particular candidate CAD location, further information about the location is displayed. The further information may be an enlarged image or one or more images sized to fit on the monitor without images for other candidate locations. For example, the images shown in FIG. 2 for a candidate location replace the summary information. As another example, the larger images are generated on a different display in response to selection of the candidate CAD locations. FIG. 6 shows two cross-sectional images on a right monitor for the candidate CAD location selected from the summary on the left monitor. Larger views of at least a subset of the images from the gallery are presented on an adjacent display in response to selection of one or more of the images. The larger views may allow a user to better diagnose the possible polyp.

For example, images for two candidate CAD locations are enlarged sequentially. One may be for a sessile polyp and another one for a pendunculated polyp. Enlarged or larger images that virtually "dissect" the polyps may reveal the type of core tissue. Enlarged or larger images that display orthogonal axes may visually provide an indication of the estimated diameter and height.

In act 38, the navigation is for sorting. The order of the candidate CAD locations in the presentation may be changed. Where the candidate locations are in a report or document extending over one or more single views, the sorting may result in different candidate CAD locations being on different pages.

The user may sort the table according to any of the available columns. The candidate CAD locations may be sorted by the images, such as one of the gallery columns. Each image is matched with a library of images representing typical structures found in colonoscopy, such as tags, stool, folds, and polyps. The library image with the closest match indicates the type of feature. The candidate CAD locations are then sorted by the identified features. The quantities or characteristics may be sorted by value or label.

Sorting may allow for a quick identification of CAD marks that point to the same structure in different views. The sorting according to core tissue type may arrange the candidate CAD locations in order of suspicion as a polyp, Muscle core tissue is more suspicious than the fat core tissue. Tagged-core is to be considered more carefully in order to distinguish between tagged stool and a coated polyp. Sorting by diameter or height may also indicate suspicion, allowing a radiologist to start with the most significant findings first. Sorting by the location in the colon or the marker ID may be provided. Nested sorting may be used, such as by sorting by core tissue and sorting by diameter or height within the core tissue sort.

In act 40, the user scrolls. The summary information may include candidate CAD locations that may not fit in a single view. The candidate locations are collected and used to from one document or summary. The user scrolls through the document or summary to view the data points for the candidate CAD locations. For example, the user scrolls within a single document. As the user scrolls, different subsets of the data points for the candidate CAD locations are displayed in the current single view. As another example, tab or page scrolling is provided where each single view of the same collection or document includes different candidate CAD locations in any grouping. Some or no overlap of presentation of candidate CAD locations may be provided.

In act 42, the user selects a subset of the candidate CAD locations. In response to user navigation, the selections are received. For example, the user causes some candidate CAD locations to be highlighted and/or others to be deleted. The selected or remaining CAD locations are possible polyps after review and diagnosis by the user. One, two, or more of the candidate CAD locations are selected as polyps or possible polyps, and the other locations are indicated as being not polyps. The selection may be of the candidates not considered polyps, effectively then selecting the possible polyps.

In act 44, additional data points are displayed for the selected possible polyps. Since fewer candidate locations are to be presented due to a first pass selection by the user, more information may be presented in the same space. Alternatively or additionally, different information is presented to better inform the user regarding the remaining possible polyps for a second pass diagnosis. The additional data points are presented without data points for the non-selected candidate CAD locations.

The processor causes display of the additional data points for the subset of candidate CAD locations. These data points are presented in a combination display, such as associated with a single view including multiple data points for each of multiple candidate CAD locations. This further summary information is presented substantially simultaneously. Alternatively, the further information or data points are provided sequentially for each candidate CAD location with or without pre-computation for one, more, or all of the candidate CAD locations.

The display of the further data points may occur without the fly-through presentation for the imaging session and prior to such display. The use of the further information as collected for the subset of candidate CAD locations may be sufficient, allowing the user to avoid any fly-through examination.

Figure 8:
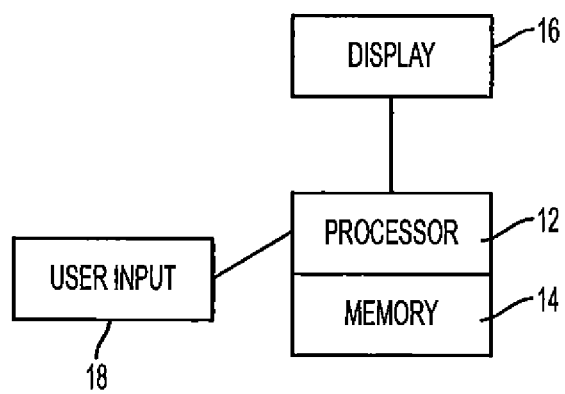
FIG. 8 is one embodiment of a system for presentation of computer assisted detection marks in medical imaging diagnosis.

FIG. 8 shows one embodiment of a system for presentation of computer assisted detection marks in medical imaging diagnosis. The system implements the method of FIG. 3 or other methods. The system includes a processor 12, memory 14, display 16, and user input 18. Additional, different or fewer components may be provided for the system. For example, a network interface allows receipt of CAD algorithm results or patient data.

In one embodiment, the system is a computer, workstation, server, or other device for presenting CAD locations to a user. For example, the system is part of a personal data assistant, cellular phone, or tablet computer. A wired or wireless connection allows access to information.

The processor 12 is a general processor, digital signal processor, server, application specific integrated circuit, field programmable gate array, digital circuit, analog circuit, combinations thereof, or other now known or later developed processor. The processor 12 is configured by software and/or hardware. The processor 12 is configured to present data points for multiple candidate CAD locations substantially simultaneously. The data points may be generated by the processor 12, such as generating and receiving the gallery images internally. In other embodiments, the data points are received from external devices and compiled by the processor 12.

The processor 12 operates as a stand alone device, such as a CAD workstation. The CAD algorithm is applied by the processor 12, and the results are presented to the user. Alternatively, the processor 12 communicates with a server or other CAD system in a cloud environment. The candidate CAD locations are received by the processor 12. The processor 12 may receive the document or summary as compiled by another device.

The processor 12 is configured to generate a summary of detected positions within a patient organ. The generation may be merely passing on the display information. Alternatively, the generation may include organizing the data points for display and passing on the organized display information. In other embodiments, the generation includes calculation of the data points, such as generation of the images, organizing of the data points, and passing on the organized display information.

The summary generated by the processor 12 may include images of the detected positions. The images are presented in a list arrangement, such as part of a table or gallery. The summary with the images is generated prior to user navigation to review specific locations in the patient organ. Prior to the user selecting a specific detected position, the summary is generated and presented to the user.

The processor 12 may be configured for other functions, such as navigation. In one embodiment, the processor 12 generates an additional summary with additional information for a subset of multiple of the detected positions. In another embodiment, the processor 12 generates or obtains and then outputs one or more enlarged images in response to user selection of one of the detected positions in the summary. These navigations and further displays may be generated without generating a flythrough presentation to the user.

The display 16 is a CRT, LCD, plasma, projector, monitor, printer, touch screen, or other now known or later developed display device. The display 16 receives the summary from the processor 12. The received summary is output on the screen of the display 16. For example, the display 16 outputs to the user images in a list arrangement where different images on the screen at any given time represent the possible polyps at different detected positions. The display may be gray scale or color image.

The user input 18 is a keyboard, mouse, track ball, touch pad, sliders, knobs, buttons, user sensor, combinations thereof, or other now known or later developed user input device. The user input 18 operates as part of a user interface in connection with the processor 12 and the display 16.

The memory 14 is a local memory for the processor 12, a separate database, a bank of RAM memory, a removable media (e.g., tapes, optical storage, reel or other now known or latter developed devices), combinations thereof or other now known or later developed memory devices. The memory 14 is configured to store candidate CAD locations, images, other data points, summaries, or combinations thereof. The memory 14 is controlled by the processor 12 for storing information prior to processing or for storing processed results.

The processor 12 may be configured, at least in part, by instructions stored on computer readable memory. The computer readable memory may be a memory local to the device, a remote memory, or the memory 14. The instructions are for presentation of computer assisted detection marks in colon computed tomography diagnosis. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many advantages and modifications can be made without departing from the scope of the invention. It is therefore intended that the foregoing detailed description be regarded as illustrative rather than limiting, and that it be understood that it is the following claims, including all equivalents, that are intended to define the spirit and the scope of this invention.

What is claimed is:

1. A method for presentation of locations in medical imaging diagnosis, the method comprising:
   first displaying, by a processor, multiple data points for each of a plurality of locations in a single view, the locations being for a same anatomy of a same patient from a same imaging session, the first displaying occurring without a prior fly-through user review of the anatomy;
   navigating, in response to user input, between the locations without the fly-through review for the imaging session occurring prior to the navigating; and
   second displaying, in response to the navigating, at least one image for a first of the locations.

2. The method of claim 1 wherein the first displaying comprises displaying a gallery of images, the gallery including multiple images for each of the locations.

3. The method of claim 1 wherein the navigating comprises jumping to the locations and bypassing other locations in the anatomy without a review of the entire anatomy.

4. The method of claim 1 wherein the first displaying occurs on a first display and the second displaying occurs on a second display.

5. The method of claim 1 wherein the first displaying comprises displaying the multiple data points as quantities for a region at the respective location.

6. The method of claim 5 wherein the first displaying also comprises displaying multiple thumbnail images as some of the data points for each of the locations.

7. The method of claim 1 further comprising:
   providing sorting of the locations in the single view by at least one of the data points.

8. The method of claim 1 further comprising:
   receiving user selection of a subset of the locations after the first displaying;
   third displaying, by the processor, additional data points for each of the locations in the subset and not for without displaying data points for locations not in the subset, the third displaying occurring in an additional single view and without the prior fly-through user review.

9. The method of claim 1 wherein first displaying comprises displaying for computer assisted detection (CAD) locations.

* * * * *